(12) United States Patent
Mashimo

(10) Patent No.: US 11,417,146 B2
(45) Date of Patent: Aug. 16, 2022

(54) IMAGE FORMING APPARATUS THAT CORRECTS IMAGE IN ACCORDANCE WITH BLOOD OXYGEN LEVEL

(71) Applicant: KYOCERA Document Solutions Inc., Osaka (JP)

(72) Inventor: Takayuki Mashimo, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 288 days.

(21) Appl. No.: 16/827,020

(22) Filed: Mar. 23, 2020

(65) Prior Publication Data
US 2020/0311383 A1 Oct. 1, 2020

(30) Foreign Application Priority Data
Mar. 28, 2019 (JP) .............................. JP2019-063955

(51) Int. Cl.
*G06V 40/12* (2022.01)
*H04N 1/00* (2006.01)
*A61B 5/02* (2006.01)

(52) U.S. Cl.
CPC ............ *G06V 40/1388* (2022.01); *A61B 5/02* (2013.01); *H04N 1/00838* (2013.01)

(58) Field of Classification Search
CPC ....... G06V 10/987; G06V 40/12–1394; G06V 40/15; G06V 40/13–1394; A61B 5/0077; A61B 5/02–0295; A61B 5/117–1178; A61B 5/14551; A61B 5/6826; A61B 2576/00; A61B 5/103–18; A61B 5/14542; A61B 5/14–1495; A61B 5/742–745; A61B 5/00838; A61B 5/1172; H04N 1/00–648; H04N 21/4415; H04N 2201/00–33392; H04N 2201/0094;
(Continued)

(56) References Cited

U.S. PATENT DOCUMENTS

2015/0112154 A1* 4/2015 He .......................... A61B 5/742
600/483
2016/0327922 A1* 11/2016 Sekiguchi ........ H04N 21/42201
(Continued)

FOREIGN PATENT DOCUMENTS

JP 2016-020933 A 2/2016

*Primary Examiner* — Amr A Awad
*Assistant Examiner* — Aaron Midkiff
(74) *Attorney, Agent, or Firm* — IP Business Solutions, LLC

(57) ABSTRACT

An image forming apparatus includes an image processing device, an image forming device, an operating device, a vital sensor, and a controller. The image processing device corrects an image. The image forming device performs an image formation of forming the image on a recording sheet. The operating device is operable by a user and through which an instruction to start the image formation by the image forming device is inputted. The vital sensor is provided at the operating device and detects a blood oxygen level of the user who is operating the operating device. The controller, when the instruction to start the image formation is inputted through the operating device, causes the image processing device to correct the image in accordance with the blood oxygen level of the user detected by the vital sensor and causes the image forming device to form a corrected image on the recording sheet.

6 Claims, 4 Drawing Sheets

(58) Field of Classification Search
CPC ... H04N 1/38–4097; H04N 1/60–6097; H04N 1/00838; G06T 5/00–50; G06T 2207/00–30268; G06F 21/32
See application file for complete search history.

(56) References Cited

U.S. PATENT DOCUMENTS

| | | | |
|---|---|---|---|
| 2017/0076182 A1* | 3/2017 | Matsuzaki | H04N 1/00023 |
| 2017/0104890 A1* | 4/2017 | Miyazaki | B41J 29/38 |
| 2017/0280018 A1* | 9/2017 | Morita | H04N 1/4433 |
| 2018/0054534 A1* | 2/2018 | Zhang | H04N 1/442 |

* cited by examiner

IMAGE FORMING APPARATUS THAT CORRECTS IMAGE IN ACCORDANCE WITH BLOOD OXYGEN LEVEL

INCORPORATION BY REFERENCE

This application claims priority to Japanese Patent Application No. 2019-63955 filed on Mar. 28, 2019, the entire contents of which are incorporated by reference herein.

BACKGROUND

The present disclosure relates to an image forming apparatus that forms an image of an original document onto a recording sheet, and particularly relates to a technique of detecting a blood oxygen level of a user and correcting, in accordance with the detected blood oxygen level, the image to be formed on the recording sheet.

At an image forming apparatus, when a user operates a start key, an image reading device reads an image of a document, an image forming device forms the image of the document on an recording sheet, then the recording sheet is discharged to a tray. Furthermore, there has been suggested an image forming apparatus provided with a UI processing device that receives contact operation of a user about an image processing and also detects biological information of the user performing the contact operation, and when the UI processing device receives the contact operation of the user, the image forming apparatus can detect and collect, by the UI processing device, the biological information belongs to the user.

SUMMARY

A technique improved over the above technique is proposed as one aspect of the present disclosure.

An image forming apparatus according to an aspect of the present disclosure includes an image processing device, an image forming device, an operating device, a vital sensor, and a controller. The image processing device performs correction on an image. The image forming device performs an image formation of forming the image on a recording sheet. The operating device is operable by a user and through which an instruction to start the image formation by the image forming device is inputted. The vital sensor is provided at the operating device and detects a blood oxygen level of the user who is operating the operating device. The controller, when the instruction to start the image formation by the image forming device is inputted through the operating device, causes the image processing device to correct the image in accordance with the blood oxygen level of the user detected by the vital sensor and causes the image forming device to form a corrected image on the recording sheet.

DETAILED DESCRIPTION

Figure 1:
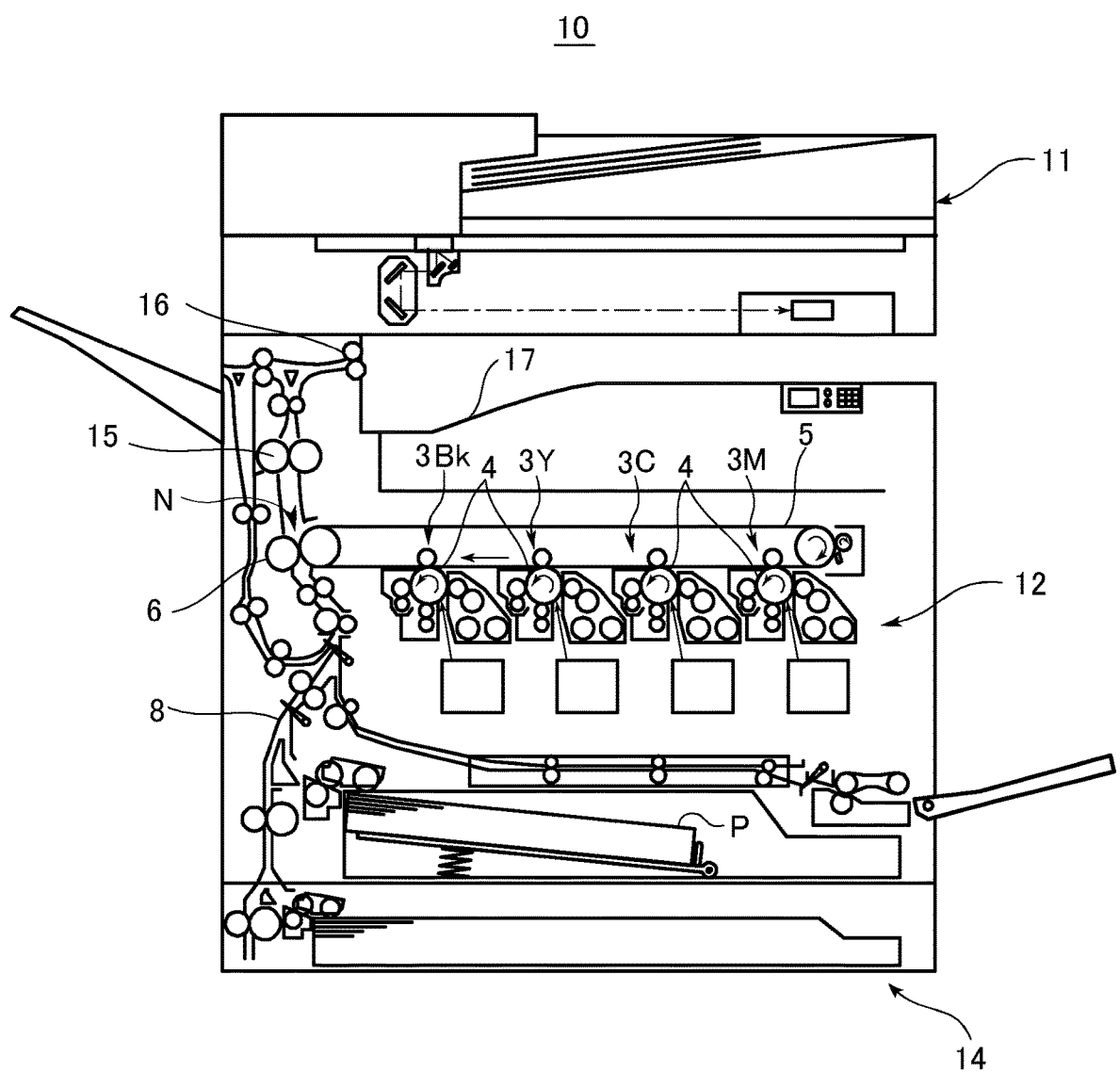
FIG. 1 is a cross-sectional view showing an image forming apparatus according to one embodiment of the present disclosure.

Hereinafter, a description will be given of an embodiment of the present disclosure, with reference to the drawings. FIG. 1 is a cross-sectional view showing the image forming apparatus according to one embodiment of the present disclosure. As FIG. 1 shows, an image forming apparatus 10 of the embodiment is a multifunction peripheral (MFP) provided with multiple functions such as a copying function, a printing function, and a facsimile transmission function. The image forming apparatus 10 includes an image reading device 11 and an image forming device 12.

The image reading device 11 includes an image pickup device that optically reads an image of a document. An analog output of the image pickup device is converted into a digital signal, from which image data representing the image of the document is generated.

The image forming device 12 performs an image formation of forming, on a recording sheet, the image represented by the image data, and includes an image forming unit 3M for magenta, an image forming unit 3C for cyan, an image forming unit 3Y for yellow, and an image forming unit 3Bk for black. In each of the image forming units 3M, 3C, 3Y, and 3Bk, a surface of a photosensitive drum 4 is uniformly charged, and an electrostatic latent image is formed on the surface of the photosensitive drum 4 by exposure. Then the electrostatic latent image on the surface of the photosensitive drum 4 is developed into a toner image, and the toner image on the photosensitive drum 4 is transferred to an intermediate transfer belt 5, as primary transfer. Thus, the color toner image is formed on the intermediate transfer belt 5. The color toner image is transferred, as secondary transfer, to a recording sheet P transported along a transport route 8 from a paper feed unit 14, at a nip region N defined between the intermediate transfer belt 5 and a secondary transfer roller 6.

Thereafter, the recording sheet P is press-heated in a fixing part 15, so that the toner image on the recording sheet P is fixed by thermal compression, and then the recording sheet P is discharged to an output tray 17 through a discharge roller pair 16.

Figure 2:
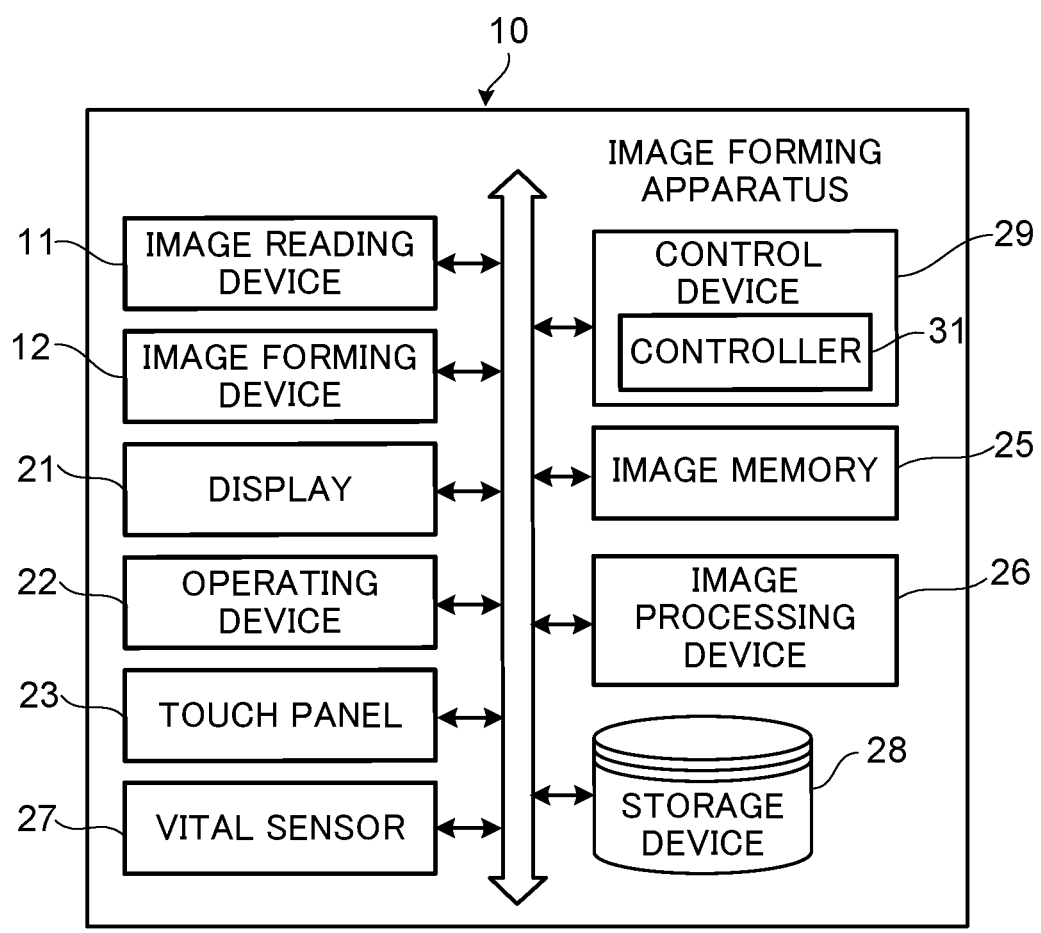
FIG. 2 is a block diagram showing main internal configurations of the image forming apparatus of the embodiment.

FIG. 2 is a block diagram showing main internal configurations of the image forming apparatus 10 of the embodiment. As shown in FIG. 2, the image forming apparatus 10 includes the image reading device 11, the image forming device 12, a display 21, an operating device 22, a touch panel 23, an image memory 25, an image processing device 26, a vital sensor 27, a storage device 28, and a control device 29. The mentioned components are configured to transmit and receive data or signals to and from each other, via a bus.

The display 21 is formed of, for example, a liquid crystal display (LCD) or an organic light-emitting diode (OLED) display.

The operating device 22 is provided with physical keys such as a numeric keypad, an enter key, and a start key.

The touch panel 23 is disposed on a screen of the display 21. The touch panel 23 is a touch panel of a so-called resistive film type or electrostatic capacity type and detects touch of the touch panel 23 by, for example, a finger of a user together with a position of the aforementioned touch, and outputs a detection signal indicating the coordinates of the position of the touch to, for example, a controller 31 (to be described later) of the control device 31. Together with the operating device 22, the touch panel 23 serves a role as an operating portion through which user operation on the screen of the display 21 is inputted.

The image data representing the image of the document read by the image reading device 11 is stored in the image memory 25. The image processing device 26 performs, on the image data stored in the image memory 25, various kinds of image processing, such as shading correction.

The vital sensor 27 is, for example, a pulse oximeter and superposedly provided below the start key provided on the operating device 22. A key cap of the start key is made of a material that transmits infrared ray and red light. The vital sensor 27 includes: light emitting parts that respectively emit, through the key cap of the start key, the infrared ray and the red light to a fingertip of the user who is pressing the start key; and a light receiving part that receives through the key cap the infrared ray and the red light that are reflected by the user's fingertip, and outputs, from the light receiving part, detection signals each corresponding to the received infrared ray and red light to the controller 31.

The storage device 28 is a large-capacity storage medium such as a solid state drive (SSD) and a hard disk drive (HDD), and contains various application programs and various types of data.

The control device 29 is formed of a processor, a random access memory (RAM), a read only memory (ROM), and so on. The processor is, for example, a central processing unit (CPU), an application specific integrated circuit (ASIC), or a micro processing unit (MPU). The control device 29 functions as the controller 31 through the processor executing a control program stored in the ROM or the storage device 28.

The controller 31 collectively controls the image forming apparatus 10. The control device 29 is connected to the image reading device 11, the image forming device 12, the display 21, the operating device 22, the touch panel 23, the image memory 25, the image processing device 26, the vital sensor 27, and the storage device 28. The controller 31 controls operation of those components and performs transmission and reception of signals or data among those components.

The controller 31 serves a role as a processing unit that executes, for example, various processing required for the image formation by the image forming apparatus 10. In addition, based on the detection signal outputted from the touch panel 23 or operation of the physical keys provided on the operating device 22, the controller 31 receives an operation instruction inputted by the user. Furthermore, the controller 31 has a function of controlling a display operation of the display 21.

The controller 31 also inputs the detection signals respectively corresponding the infrared ray and the red light outputted from the above-described light receiving part of the vital sensor 27, and based on the detection signals, the controller 31 calculates a blood oxygen level of the fingertip of the user who is pressing the start key provided on the operating device 22.

On the image forming apparatus 10 having the configurations as described above, the user operates the operating device 22 or the touch panel 23 to input user's own identification information ID. Upon authenticating the identification information ID, the controller 31 permits the user of that identification information ID to use the image forming apparatus 10. When the user sets a document on the image reading device 11 and operates the start key provided on the operating device 22 to instruct execution of copying, the controller 31 causes the image reading device 11 to read an image of the document, and causes the image memory 25 to store the image data representing the image of the document. The image processing device 26 performs various kinds of processing on the image data. The image forming device 12 inputs the image data from the image memory 25 and forms the image of the document represented by the image data on the recording sheet.

Every time the start key is operated, the controller 31 calculates, based on the detection signals respectively corresponding the infrared ray and the red light, which are outputted from the light receiving part of the vital sensor 27, the blood oxygen level of the fingertip of the user who is pressing the start key, and causes the storage device 28 to store the blood oxygen level in association with the identification information ID of the user. Then when the start key provided on the operating device 22 is operated again and the controller 31 calculates, based on the detection signal outputted from the vital sensor 27, the blood oxygen level of a fingertip of the user who is pressing the start key, reads out past blood oxygen levels associated with the identification information ID of the user from the storage device 28, calculates an average value of the past blood oxygen levels, compares, with the average value, the blood oxygen level calculated this time at the operation of the start key, and instructs the image processing device 26 to perform, on the image data, correction in accordance with a result of the comparison. The image processing device 26 performs, on the image data stored in the image memory 25, the correction in accordance with the comparison result. For example, when the blood oxygen level calculated this time at the operation of the start key is lower than the average value, for the user is in a poor physical condition, the image processing device 26, by the correction on the image data, limits the hue, lightness, or saturation of the image represented by the image data to give a calm impression to the image, or makes the image easier to see by increasing the size of the image represented by the image data.

To be more specific, as the correction on the image in accordance with the comparison result, when the blood oxygen level calculated this time at the operation of the start key is lower than the average value, the image processing device 26 performs either (i) change the hue of the image to a predetermined warm color, (ii) decrease the brightness of the image by a predetermined value, (iii) reduce the saturation of the image by a predetermined value, and (iv) increase the size of the image by a predetermined amount.

Accordingly, the image formed on the recording sheet by the image forming device 12 is to be the image corrected in accordance with the blood oxygen level of the user who pressed the start key.

Figure 3:
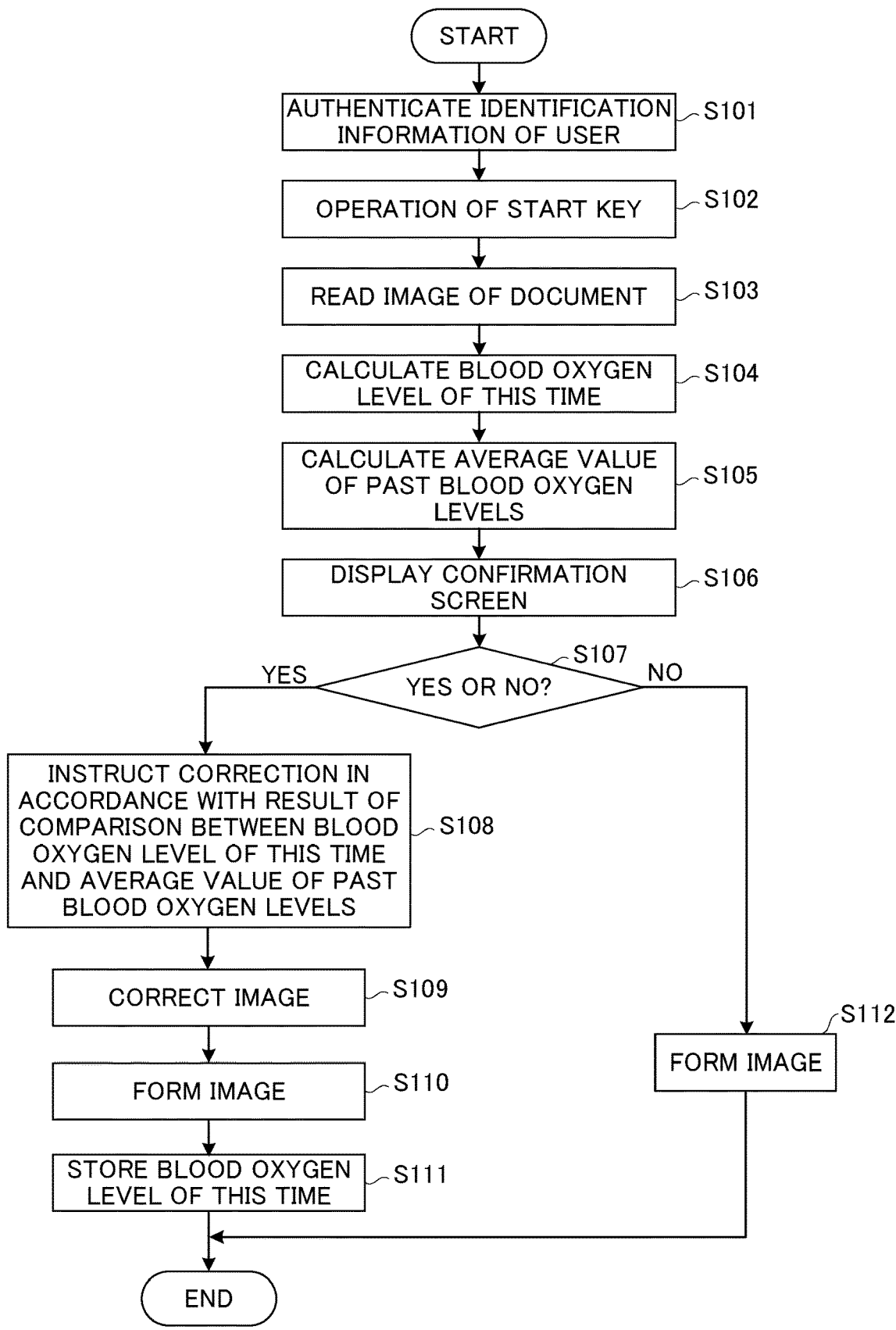
FIG. 3 is a flowchart showing processing procedures for detecting a blood oxygen level of a user and correcting, in accordance with the detected blood oxygen level, an image to be formed on a recording sheet.

With reference to a flowchart shown in FIG. 3 and so on, hereinafter describes in detail processing procedures for detecting the blood oxygen level of the user and for correcting the image to be formed on the recording sheet in accordance with the blood oxygen level as described above.

Firstly, the user operates the operating device 22 or the touch panel 23 of the image forming apparatus 10 to input the user's own identification information ID. On the image forming apparatus 10, upon entry of the identification information ID of the user, the controller 31 authenticates the identification information ID of the user and permits the user of that identification information ID to use the image forming apparatus 10 (S101).

The user then sets a document on the image reading device 11 and operates the start key provided on the operating device 22 to instruct execution of copying. Upon receiving the operation of the start key (S102), the controller 31 causes the image reading device 11 to read an image of the document and the image memory 25 to store the image data representing the image of the document (S103).

At the same time, based on the detection signals respectively corresponding the infrared ray and the red light outputted from the light receiving part of the vital sensor 27, the controller 31 calculates the blood oxygen level of the fingertip of the user who is pressing the start key (S104). The controller 31 also reads out the past blood oxygen levels associated with the identification information ID of the user who has been authenticated in the step S101 from the storage device 28, and calculates the average value of the past blood oxygen levels (S105).

Figure 4:
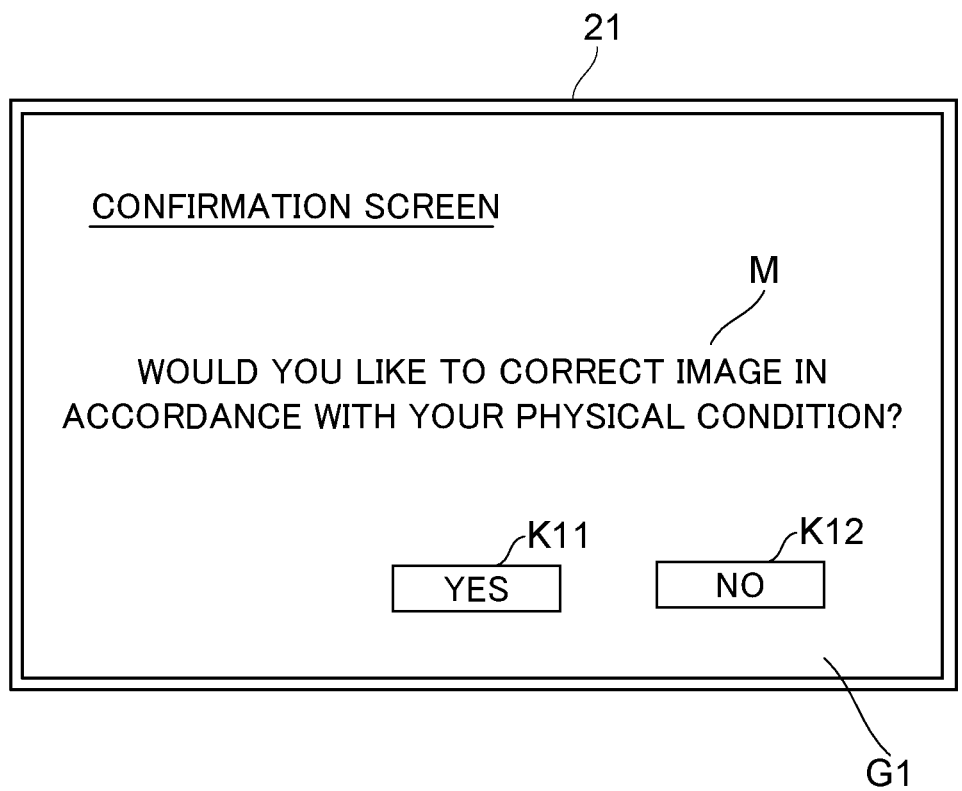
FIG. 4 is a view showing a confirmation screen displayed on a display of the image forming apparatus.

Then, the controller 31 causes the display 21 to display a confirmation screen G1 shown in FIG. 4 (S106). The confirmation screen G1 shown in FIG. 4 includes a message M asking whether to correct the image, together with an YES key K11 and a NO key K12. The user sees the message M1 on the confirmation screen G1, and then touches either the YES key K11 or the NO key K12.

For example, when the user touches the YES key K11 to instruct to correct the image, the controller 31 receives an image correction execution instruction through the touch panel 23 (YES in S107). In this case, the controller 31 compares the blood oxygen level calculated in the step S104 with the average value calculated in the step S105, and instructs the image processing device 26 to perform, on the image data, correction in accordance with the comparison result (S108). The image processing device 26 performs, on the image data stored in the image memory 25, the correction in accordance with the comparison result (S109). The image forming device 12 forms the image of the document represented by the image data stored in the image memory 25 on the recording sheet (S110). For example, when the blood oxygen level calculated in the step S104 is lower than the average value calculated in the step S105, the image processing device 26 corrects the image data and gives the calm impression to the image represented by the image data or increase the size of the image represented by the image data. The corrected image is recorded on the recording sheet. Specifically, as the correction on the image in accordance with the comparison result, when the blood oxygen level calculated this time at the operation of the start key is lower than the average value, the image processing device 26 performs either of the above-described processing (i) to (iv).

Thereafter the controller 31 associates the blood oxygen level calculated in the step S104 with the identification information ID of the user having been authenticated in the step S101 and adds to the storage device 28 to be stored therein, then updates the blood oxygen levels associated with the identification information ID of the user (S111).

When the user touches the NO key K12, the controller 31 receives an image correction non-execution instruction through the touch panel 23 ("NO" in S107), and, without performing the processing in the steps S108 and S109 (thus, without performing the correction in accordance with the aforesaid comparison result by the image processing device 26 on the image data stored in the image memory 25), causes the image of the document represented by the image data to be formed on the recording sheet (S112).

As thus far described, in this embodiment, when the start key provided on the operating device 22 is operated, the blood oxygen level of the fingertip of the user who is pressing the start key is calculated based on the detection signal outputted from the vital sensor 27, the average value of the past blood oxygen levels of the user is also calculated, the blood oxygen level calculated this time at the operation of the start key is compared with the average value, the correction in accordance with the comparison result is performed on the image data stored in the image memory 25, and the image represented by the image data is formed on the recording sheet. Thereby, in accordance with the physical condition of the user, the color or the size of the image formed on the recording paper is adjusted.

It can be suggested to adjust the color, size, and so on of the image formed on the recording sheet in accordance with the physical condition of the user. For example, when the user is tired, it is desirable to make the color of the image calm or to increase the size of the image. Among commonly used image forming apparatuses, there are ones that, when UI processing devices receive contact operation of users, detect and collect the contact operation of users at the UI processing devices. However, colors and sizes of the images are not adjusted in accordance with the collected pieces of biological information belong to the users. In contrast, according to the present embodiment, the image to be formed on the recording sheet can be corrected in accordance with the physical condition of the user.

It is difficult to accurately estimate the physical condition of the user based only on the temporary blood oxygen level because the blood oxygen level varies due to individuals, genders, ages, and so on. In the present embodiment, however, the blood oxygen level calculated this time at the operation of the start key is compared with the average value of the past blood oxygen levels of the user, and because the average value is used as a standard value of the user on which differences due to individuals, genders, ages, and so on are reflected, the physical condition of the user can be more accurately estimated based on the comparison of the blood oxygen level calculated this time with the average value.

In the above embodiment, the user operates the operating device 22 or the touch panel 23 to input the user's own identification information ID. However, the image forming apparatus 10 may be provided with an ID card reader, and it may be configured such that the ID card reader reads the identification information ID from an ID card of the user.

Alternatively, a fingerprint sensor may be provided below the key cap of the start key together with the vital sensor 27, and it may be configured such that, when the start key is operated, the fingerprint sensor detects a fingerprint of the user as the identification information of the user, and the controller 31 identifies the user based on the detected fingerprint of the user. In such case, a single operation of the start key can allow three processing, such as instructing the start of the image formation, detecting the blood oxygen level, and identifying the user, to be performed.

In the above-described embodiment, the blood oxygen level calculated this time at the operation of the start key is compared with the average of the past blood oxygen levels, and the correction in accordance with the result of the comparison is performed on the image data stored in the image memory 25. It may further be configured such that, when the blood oxygen level calculated this time at the operation of the start key is lower than a predetermined threshold value, it is regarded that the physical condition of the user is becoming poor, and the controller 31 causes the image processing device 26 to correct the image data stored in the image memory 25.

<Variation 1>

In Variation 1, every time the start key is operated, the controller 31 calculates, based on the detection signal outputted from the vital sensor 27, the blood oxygen level of the fingertip of the user who pressed the start key, and causes the storage device 28 to store the blood oxygen level in association with the identification information ID of the user. Then when the start key provided on the operating device 22 is operated again, the controller 31 calculates, based on the detection signal outputted from the vital sensor 27, the blood oxygen level of the fingertip of the user, reads out the past blood oxygen levels of the user associated with the identification information ID from the storage device 28, calculates a time-serial change of the past blood oxygen levels and the blood oxygen level calculated this time at the operation of the start key (an amount of change in these blood oxygen levels), and instructs the image processing device 26 to perform correction in accordance with the change on the image data. The image processing device 26 performs, on the image data stored in the image memory 25, the correction in accordance with the change. To be more specific, as the correction on the image in accordance with the time-serial change, when the amount of change in the blood oxygen levels of the user read out and the blood oxygen level detected again is on a downward trend, the image processing device 26 performs either (i) change the hue of the image to a predetermined warm color, (ii) decrease the brightness of the image by a predetermined value, (iii) reduce the saturation of the image by a predetermined value, and (iv) increase the size of the image by a predetermined amount. The image forming device 12 forms the image represented by the corrected image data on the recording sheet.

For example, when the blood oxygen level has recently been on a downward trend, it is regarded that the physical condition of the user is becoming poor, and the controller 31 corrects the hue, brightness or saturation of the image to give the calm impression to the image, or makes the image easier to see by increasing the size of the image.

<Variation 2>

In Variation 2, when the start key is operated, based on the detection signal outputted from the vital sensor 27, the controller 31 calculates the blood oxygen level of the fingertip of the user and also inputs or determines the age of the user, then instructs the image processing device 26 to perform on the image data correction in accordance with the calculated blood oxygen level and the age of the user.

For example, the controller 31 previously stores in the storage device 28, by age, a standard blood oxygen level of each age. The controller 31 reads out, from the storage device 28, the blood oxygen level at the inputted or determined age, compares the blood oxygen level of the fingertip of the user and the blood oxygen level at the inputted or determined age, and instruct the image processing device 26 to perform the correction in accordance with the result of the comparison. The image processing device 26 performs the correction on the image data stored in the image memory 25. The controller 31 causes the image forming device 12 to form the image represented by the corrected data on the recording sheet.

As a result, it is possible to correct the image accurately while suppressing the effect of the age difference in the blood oxygen level.

The age of the user may be inputted through the user operating the operating device 22 or the touch panel 23. The controller 31 acquires the age of the user inputted by the operation on the operating device 22 or on the touch panel 23.

Alternatively, the image forming apparatus 10 may be provided with the ID card reader, and it may be configured such that the ID card reader reads the identification information ID, the user's age, date of birth, and so forth from the ID card of the user. The controller 31 acquires the user's age read from the ID card or calculates the age based on the user's date of birth read from the ID card.

Furthermore, the fingerprint sensor may be provided below the key cap of the start key together with the vital sensor 27, and it may be configured such that, when the start key is operated, the fingerprint sensor detects the fingerprint of the user as the identification information of the user, and the controller 31 acquires the age of the user associated beforehand with the detected user's fingerprint.

Still further, an image pickup camera may be provided at the image forming apparatus 10, and it may be configured such that the controller 31 cause the image pickup camera to pick-up a face image of the user to determine the age of the user based on the face image. The determination of the age of a person based on this face image may be performed by a method using a known artificial intelligent and the like.

<Variation 3>

In Variation 3, the controller 31 causes the display 21 to display a warning message corresponding to the blood oxygen level of the fingertip of the user who is pressing the start key.

For example, when the start key provided on the operating device 22 is operated, the controller 31 calculates the blood oxygen level of the fingertip of the user based on the detection signal outputted from the vital sensor 27, and when the blood oxygen level is lower than the predetermined threshold value, the controller 31 causes the display 21 to display the warning message denoting that the user is in a poor physical condition.

Alternatively, when the start key provided on the operating device 22 is operated, the controller 31 calculates the blood oxygen level of the fingertip of the user based on the detection signal outputted from the vital sensor 27, reads out the past blood oxygen levels associated with the identification information ID of the user from the storage device 28, and when the blood oxygen level this time is lower than the average of the past blood oxygen levels or when it is found that, with reference to the time-serial change of the past blood oxygen levels and the blood oxygen level this time, the blood oxygen level of the user is recently on a downward trend, causes the display 21 to display the warning message.

<Variation 4>

In Variation 4, the controller 31 corrects the image being displayed on the display 21 in accordance with the blood oxygen level of the fingertip of the user who is pressing the start key.

For example, when the start key provided on the operating device 22 is operated, the controller 31 calculates the blood oxygen level of the fingertip of the user based on the detection signal outputted from the vital sensor 27, and when the blood oxygen level is lower than the predetermined threshold value, the controller 31 limits the hue, lightness, or saturation of the image being displayed on the display 21 to give a calm impression to the image, or makes the image easier to see by increasing the size of the image.

Alternatively, when the start key provided on the operating device 22 is operated, the controller 31 calculates the blood oxygen level of the fingertip of the user based on the detection signal outputted from the vital sensor 27, reads out the past blood oxygen levels associated with the identification information ID of the user from the storage device 28, and when the blood oxygen level this time is lower than the average of the past blood oxygen levels or when it is found that, with reference to the time-serial change of the past blood oxygen levels and the blood oxygen level this time, the blood oxygen level of the user is recently on a downward trend, limits the hue, lightness, or saturation of the image being displayed on the display 21 to give a calm impression to the image, or makes the image easier to see by increasing the size of the image.

Although the descriptions have been given by using the image forming apparatus (MFP) in the above embodiment and the variations, the example is merely illustrative. Other image forming apparatus such as a copier, a printer, a facsimile machine, and so on may be used.

The configuration and processing of the above embodiments described with reference to FIGS. 1 to 4 are merely illustrative of the present disclosure and not intended to limit the present disclosure to the above particular configuration and processing.

While the present disclosure has been described in detail with reference to the embodiments thereof, it would be apparent to those skilled in the art the various changes and modifications may be made therein within the scope defined by the appended claims.

What is claimed is:

1. An image forming apparatus comprising:
an image processing device that performs correction on an image;
an image forming device that performs an image formation of forming the image on a recording sheet;
an operating device that is operable by a user and through which an instruction to start the image formation by the image forming device is inputted;
a vital sensor that is provided at the operating device and detects a blood oxygen level of the user who is operating the operating device; and
a controller that, when the instruction to start the image formation by the image forming device is inputted through the operating device, causes the image processing device to correct the image in accordance with the blood oxygen level of the user detected by the vital sensor and causes the image forming device to form a corrected image on the recording sheet,
wherein the image forming apparatus further comprising:
an input device through which identification information of the user is inputted; and
a storage device,
wherein every time the identification information of the user is inputted through the input device and the blood oxygen level of the user is detected by the vital sensor, the controller causes the storage device to store the blood oxygen level of the user in association with the identification information of the user, and when the identification information of the user is inputted again through the input device and the blood oxygen level of the user is detected again by the vital sensor, the controller reads out from the storage device blood oxygen levels of the user associated with the identification information of the user inputted again, calculates an average value of the blood oxygen levels of the user read out, compares the blood oxygen level detected again and the average value, and causes the image processing device to correct the image in accordance with a result of the comparison,
wherein when the blood oxygen level detected again is lower than the average value, as the correction on the image in accordance with the result of the comparison, the image processing device performs either (i) change a hue of the image to a predetermined warm color, (ii) decrease a brightness of the image by a predetermined value, (iii) reduce a saturation of the image by a predetermined value, and (iv) increase a size of the image by a predetermined amount.

2. The image forming apparatus according to claim 1, wherein the input device is a fingerprint sensor that detects and inputs a fingerprint of the user as the identification information of the user.

3. The image forming apparatus according to claim 1, further comprising a display,
wherein the controller causes the display to display an inquiry message asking whether or not to perform the correction on the image by the image processing device, and corrects the image by the image processing device when an instruction to correct the image is performed.

4. The image forming apparatus according to claim 1, further comprising a display,
wherein when the blood oxygen level of the user detected by the vital sensor is lower than a predetermined threshold value, the controller causes the display to display a warning message denoting that the user is in a poor physical condition.

5. The image forming apparatus according to claim 1, further comprising a display,
wherein the controller corrects an image being displayed on the display in accordance with the blood oxygen level of the user detected by the vital sensor.

6. An image forming apparatus comprising:
an image processing device that performs correction on an image;
an image forming device that performs an image formation of forming the image on a recording sheet;
an operating device that is operable by a user and through which an instruction to start the image formation by the image forming device is inputted;
a vital sensor that is provided at the operating device and detects a blood oxygen level of the user who is operating the operating device; and
a controller that, when the instruction to start the image formation by the image forming device is inputted through the operating device, causes the image processing device to correct the image in accordance with the blood oxygen level of the user detected by the vital sensor and causes the image forming device to form a corrected image on the recording sheet,
wherein the image forming apparatus further comprising:
an input device through which identification information of the user is inputted; and
a storage device,
wherein every time the identification information of the user is inputted through the input device and the blood oxygen level of the user is detected by the vital sensor, the controller causes the storage device to store the blood oxygen level of the user in association with the identification information of the user, and when the identification information of the user is inputted again through the input device and the blood oxygen level of the user is detected again by the vital sensor, the controller reads out from the storage device blood oxygen levels of the user associated with the identification information of the user inputted again, and causes the image processing device to correct the image in accordance with a time-serial change of the blood oxygen levels of the user read out and the blood oxygen level detected again,
wherein when an amount of change in the blood oxygen levels of the user read out and the blood oxygen level detected again is on a downward trend, as the correction on the image in accordance with the time-serial change, the image processing device performs either (i) change a hue of the image to a predetermined warm color, (ii) decrease a brightness of the image by a predetermined value, (iii) reduce a saturation of the image by a predetermined value, and (iv) increase a size of the image by a predetermined amount.

* * * * *